United States Patent
Hunter et al.

(10) Patent No.: US 6,236,884 B1
(45) Date of Patent: *May 22, 2001

(54) SYSTEM FOR RECORDING STIMULI AND A PLURALITY OF TEST SUBJECT'S RESPONSE TO THE STIMULI

(75) Inventors: David B. Hunter, King of Prussia; Kenneth B. McCarraher, Pottstown; Richard M. Brueggman, Bethel Park; Tomas J. Stenstrom, Ft. Washington; Harlan I. Gustafson, Jr., Limerick, all of PA (US)

(73) Assignee: Capita Research Group Inc., Blue Bell, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/357,959

(22) Filed: Jul. 21, 1999

(51) Int. Cl.[7] ........................................................ A61B 5/04
(52) U.S. Cl. ................................................................ 600/544
(58) Field of Search ..................................... 600/544, 546, 600/300, 26, 27, 28

(56) References Cited

U.S. PATENT DOCUMENTS

| 4,955,388 | * | 9/1990 | Silberstein | 600/544 |
| 5,392,788 | * | 2/1995 | Hudspeth | 600/544 |
| 5,495,853 | * | 3/1996 | Yasushi | 600/545 |
| 5,762,611 | * | 6/1998 | Lewis et al. | 600/544 |
| 6,007,569 | * | 12/1999 | Frenkel et al. | 607/88 |

* cited by examiner

*Primary Examiner*—John P. Lacyk
(74) *Attorney, Agent, or Firm*—Oblon, Spivak, McClelland, Maier & Neustadt, P.C.

(57) ABSTRACT

A system to integrate and synchronize a plurality of signals for recording on a destination video recording device and/or for display on a monitor. The plurality of signals represent the response of a respective of a plurality of test subjects to certain stimuli. A plurality of test subjects view an audio-visual display from an audio-video source, such as a video cassette recorder, while respective EEG responses to the audio-video display are measured. The respective EEG responses are sent to respective processors and converted to graphical representations of the EEG signals. The graphical representations of the EEG signals and a signal from the source audio-video device are sent to respective destination VCRs and/or a respective destination audio-video recording device that records the data from both sources. The respective destination audio-video recording devices can send respective composite signals to a respective destination VCR and/or a respective destination monitor to record and/or display the synchronized signals from the source audio-video recording device and the graphical representation of the EEG signals simultaneously. The respective destination VCRs and respective destination monitors can also record and/or display output and control data such as the time and date of the test.

32 Claims, 5 Drawing Sheets

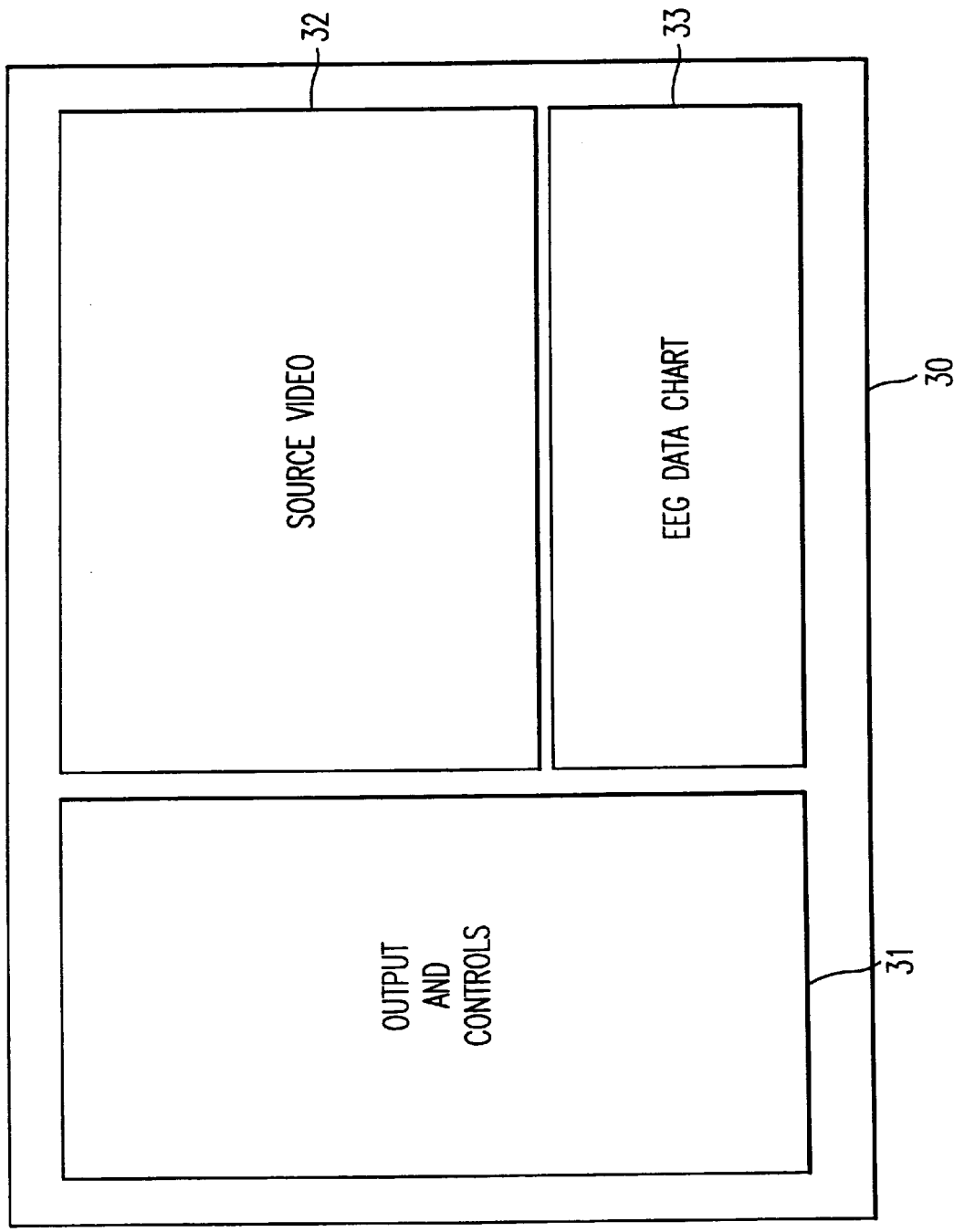

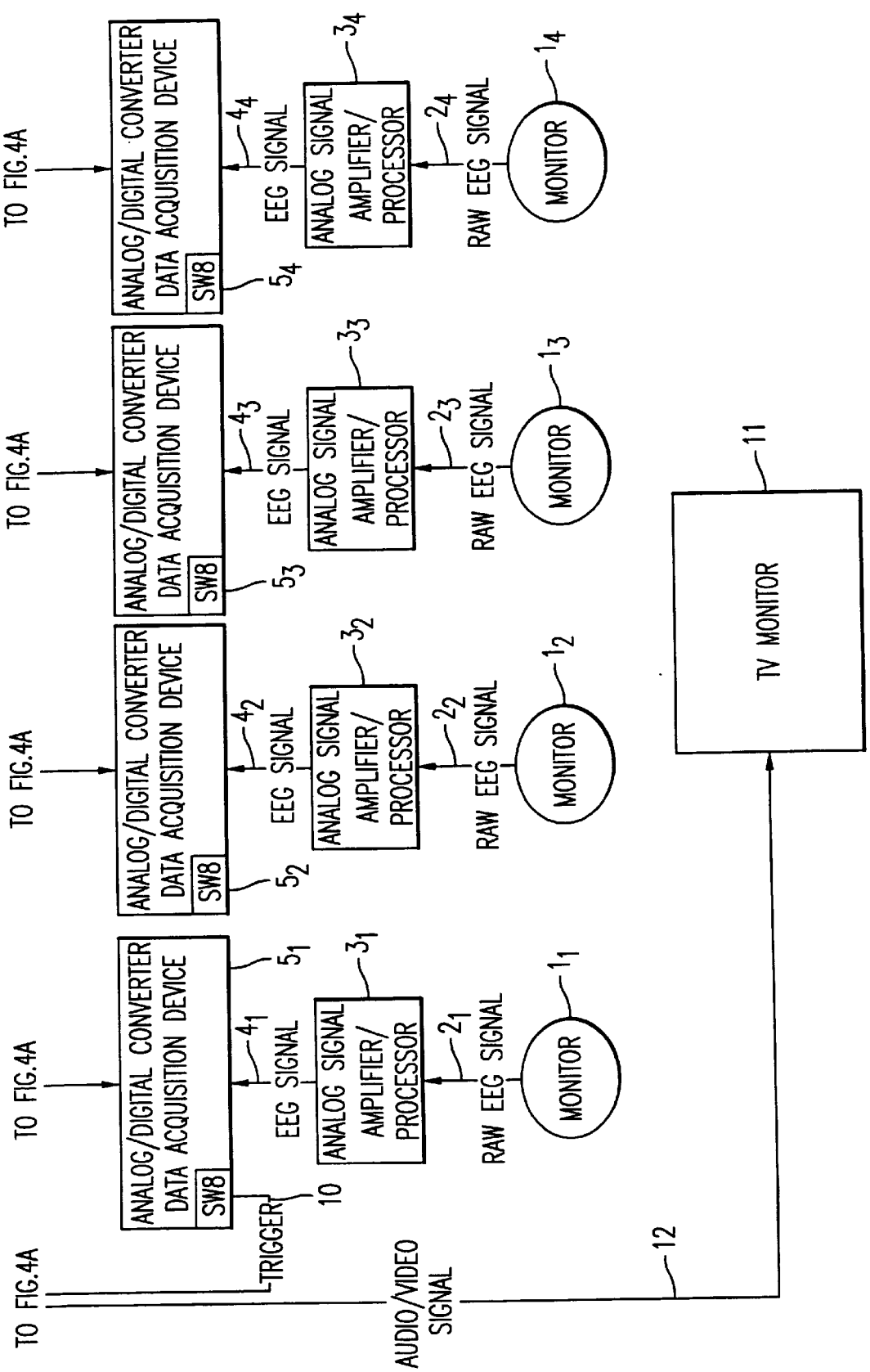

SYSTEM FOR RECORDING STIMULI AND A PLURALITY OF TEST SUBJECT'S RESPONSE TO THE STIMULI

CROSS-REFERENCE TO RELATED APPLICATIONS

This document is related to U.S. patent application Ser. No. 09/343,524, the entire contents of which are hereby incorporated by reference.

BACKGROUND OF THE INVENTION

1. Field of the Invention

The present invention is directed to a system which subjects a test subject or test subjects to certain stimuli, measures a reaction of the test subject or subjects to the stimuli, and subsequently overlappingly records and/or displays in parallel data of both the stimuli and the respective test subject's reaction to the stimuli in synchronization. The recorded data can also then be displayed or replayed to evaluate the test subject's reaction to the stimuli. Test data from a plurality of test subjects can thus be simultaneously recorded and/or stored in parallel.

2. Discussion of the Background

It is often desirable to monitor how a person reacts to certain stimuli, such as an audio presentation, a video presentation, etc. The different ways of monitoring how a patient reacts to such stimuli may be by taking an EKG of the patient, an EEG of the patient, heart rate, etc. As one concrete example, it is often desirable to take EEG measurements of a test subject to determine the brain activity of the test subject. There are many medical applications that require testing and measuring of EEG signals to determine a test subject's medical condition. There are also instances in which it is desirable to measure a test subject's brain activity for other purposes.

One such purpose is to monitor a test subject's brain activity to measure the test subject's reaction or interest to certain stimuli. For example, it may be desirable to be able to measure a test subject's attention level to a particular marketing idea, television commercial, presentation, etc.

One problem with measuring a subject's response to certain stimuli and effectively using that data to provide a meaningful graphical representation of the subject's responses to the certain stimuli occurs when the test giver attempts to accurately correlate the subjects response to the stimuli.

That is, after, as one example, an EEG measurement is taken of a test subject, this data must be evaluated relative to the stimuli to which the test subject was subjected. This is often a very difficult and time consuming operation since it is often very difficult to correspond the test subject's reaction as indicated in the EEG data obtained from monitoring the test subject, with the stimuli to which the test subject was subjected.

SUMMARY OF THE INVENTION

The Applicant's of the present invention have recognized that in the above-discussed type of analysis, it would be beneficial to synchronize the test subject's response to stimuli along with the stimuli in an integrated overlapping display and/or recording that would enable a person reviewing the test data to observe on a single display both the graphical representation of the test subject's response and the stimuli to which the test subject is responding.

It may also be desirable to integrate into the displayed results other data relating to the test conditions. This data could include, but is not limited to, test parameters such as time and date of the test, demographic data relating to the test subject, and other control data related to the test.

The Applicant's of the present invention have thus further recognized that there is a need for a system and method to accurately synchronize on a single display and/or recording a graphical representation of a test subject's response to stimuli, a display of the stimuli to which the subject is responding, and other data relating to test parameters.

The Applicants of the present invention have further recognized that it may be beneficial to obtain test data from a plurality of test subjects responding to the same stimuli in parallel. This would allow a test giver to obtain test data from a plurality of test subjects response to the same stimuli in a very short period of time.

OBJECTS OF THE INVENTION

Therefore, it is an object of this invention to provide a novel system and method to accurately overlap and synchronize on a single display and/or recording a graphical representation of a test subject's response to stimuli and the stimuli to which the subject is responding. The single display and/or recording may also include, if desired, other data relating to test parameters.

It is another object of this invention to provide a novel system and method to easily and efficiently allow for the display and/or recording with minimum input needed from an operator.

The present invention is directed to a system which can subject a test subject to certain stimuli, detect the test subject's response to the stimuli, and then display and/or record in synchronization the stimuli to which the test subject was subjected, and the test subject's detected response to that stimuli. The recorded data can then also be replayed, displayed, etc.

A further object of the present invention is to record as a data file the overlapped and synchronized graphical representation of a test subject's response to stimuli and the stimuli to which the test subject is responding. This recorded data can then be synthesized and processed with other data as desired.

A further object of the present invention is to provide a novel system and method to easily and efficiently allow for the display and/or recording of stimuli and a plurality of test subject's response to that stimuli in parallel.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 3 illustrates a preferred embodiment of on output display of the present invention.

DESCRIPTION OF THE PREFERRED EMBODIMENTS

Figure 1:
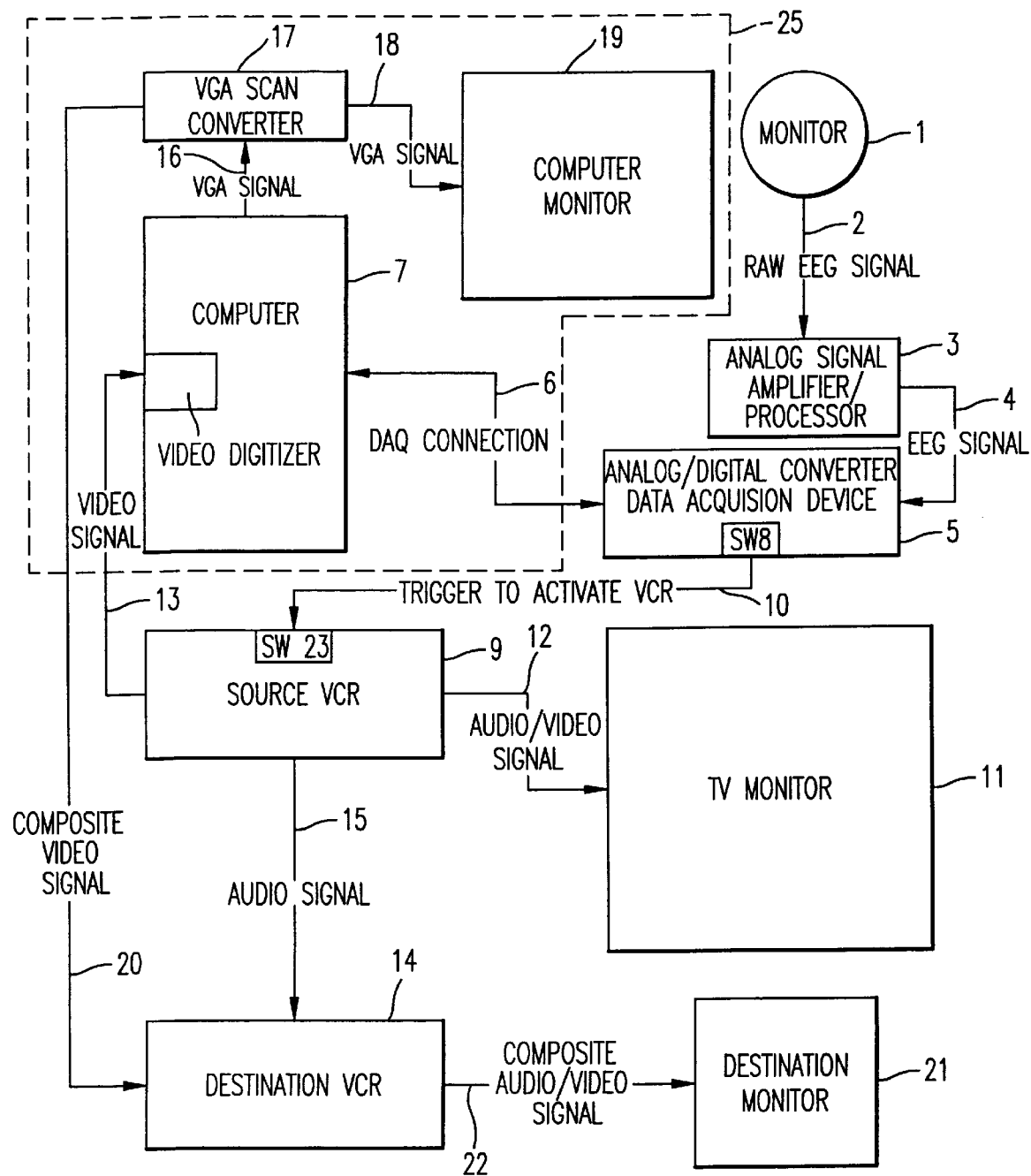
FIG. 1 illustrates a preferred embodiment of the present invention showing hardware components of the system of the present invention.
Figure 2:
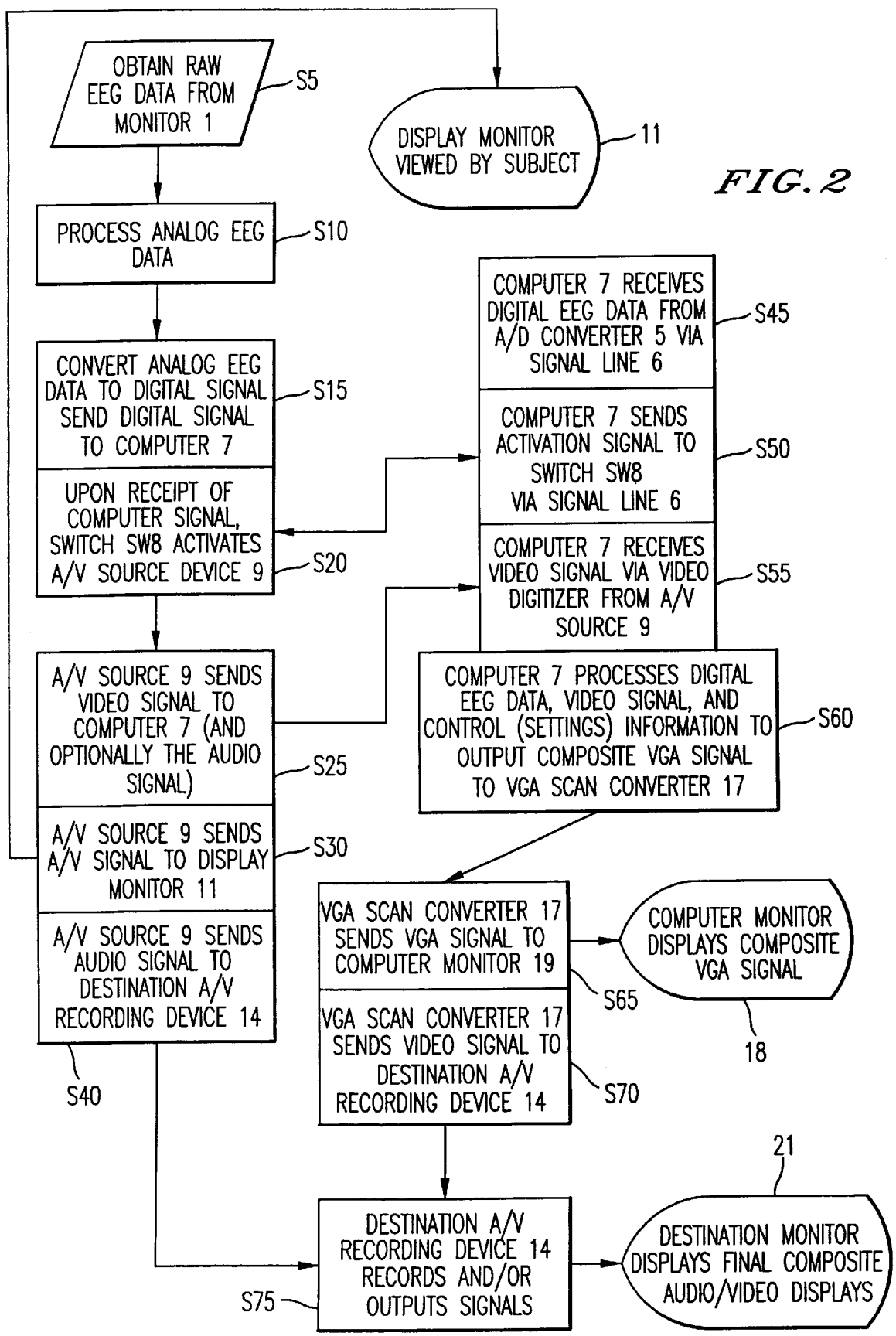
FIG. 2 illustrates a flow chart showing processing of signals to obtain a synchronized and overlapping output display.

FIG. 1 illustrates the components of a preferred embodiment of the system of the present invention used to provide precisely synchronized and overlapped output test data which represents a test subject's response to certain stimuli, the certain stimuli, and if desired other control data and parameters, and FIG. 2 shows the control steps executed in the system.

The present invention is directed to a system which can subject a test subject to certain stimuli, detect the test subject's response to the stimuli, and then display and/or overlappingly record in synchronization the stimuli to which the test subject was subjected, and the test subject's detected response to that stimuli. This recorded data can then also be replayed, further processed, displayed, etc.

The Applicants of the present invention anticipate widespread uses for such a system as in the present invention. One envisioned use of the system of the present invention is to measure a person's level of engagement to a video presentation, such as an advertisement, a speech, a sales pitch, etc. In these envisioned uses of the present invention, a test subject is shown a video presentation, and as the test subject is viewing the video presentation, EEG data of the test subject is detected. Then, the system of the present invention records and/or displays the video presentation which the test subject is viewing along with the detected EEG data in synchronization, for example on a video tape.

This operation in the present invention provides a video tape which shows both a video presentation which a test subject viewed along with the test subject's EEG response to that video presentation. The result of this is that someone evaluating the video presentation can easily and efficiently know which points of the video presentation elicited certain engagement activity from the test subject. For example, a person evaluating the video data can evaluate precisely at which portions of the video presentation the test subject was most engaged and at which portions of the video presentation the test subject was least engaged. This data is easily and quickly discernable to someone viewing the video data because the video presentation is displayed simultaneously and in synchronization with the test subject's EEG data.

The example noted above provides an example of a video presentation and measuring a test subject's level of engagement, i.e., generating EEG data. The present invention can also be applied to other stimuli, such as an audio presentation, in which case the recorded data will synchronize the audio presentation with the EEG data, which can still be displayed. Other stimuli and other measures of a test subject's response to the stimuli, such as EKG data, heart rate data, blood pressure, body temperature, galvanic skin response, pupil dilation, etc., can also clearly be instituted.

The following described preferred embodiment of the present invention is directed to the example noted above of a test subject viewing a video presentation and detecting EEG data from the test subject, although again as noted above other stimuli and other responses are clearly possible.

In the preferred embodiment of the present invention as noted above, EEG data of a test subject must be obtained. This can be done by monitoring a test subject in any known way. The Applicants of the present invention have devised a novel way of easily and efficiently monitoring a test subject to detect EEG data, which is disclosed in copending U.S. application Ser. No. 09/187,525, the entire contents of which are hereby incorporated by reference. The present invention is not limited to such a system of monitoring a subject to obtain EEG data, and the present invention can be applied to any system which monitors a subject to obtain such data or similar desired data.

The present invention will now be described in greater detail by reference to FIGS. 1 and 2. FIG. 1 is a hardware diagram of the present invention, and FIG. 2 is a chart indicating control processes executed by the hardware of FIG. 1. In the following discussion of the operation of the present invention, reference is made to both FIGS. 1 and 2.

An overview of the operation of the system as shown in FIGS. 1 and 2 will now be given prior to describing the specific controls executed. In the system as shown in FIGS. 1 and 2, a test subject views video data on a TV monitor 11 generated from a source VCR 9. A monitor 1 detects the test subjects EEG response to viewing the video data on the TV monitor 11. The EEG data monitored from the test subject is then fed to a computer 7. In synchronization with the computer 7 receiving the EEG data from the test subject, the computer 7 also receives the video data that the test subject is viewing from the source VCR 9. That is, the source VCR 9 outputs the video data both to the TV monitor 11 and to the computer 7. The computer 7 then combines the source video data which the test subject is viewing with the EEG data generated while the test subject views the video data. The video data and the test subject's EEG response to the video data is then overlapped in synchronization and provided to a destination VCR 14 to be recorded thereon.

The end result of this process of the present invention is that a recording is made at the destination VCR 14 in which the video tape includes video data which a test subject viewed, and a synchronized display of the test subject's EEG response to that video data. Someone then evaluating the combined video data can see precisely how a test subject's EEG response varied with the video data. Someone evaluating that video tape can easily detect at exactly what scenes of the video data the test subject was more engaged, less engaged, etc.

Now the operation of the present invention is described in further detail with reference to FIGS. 1 and 2.

In the present invention, and with reference to FIG. 1, a monitor 1 is placed on a test subject (not shown) in order to measure the EEG activity of the test subject (see also step S5 in FIG. 2). The monitor 1 can be the headset of Applicants' copending U.S. application Ser. No. 09/187,525, but is not limited to such. The test subject will be viewing video data on the TV monitor 11, and the monitor 1 provides a raw EEG signal based on the test subject's response to viewing the video data on the TV monitor 11. The raw EEG signal data obtained from the monitor 1 is then input through signal line 2 to an analog signal processor 3 that processes the raw EEG signal into a form that can be further processed into a meaningful representation of the subject's responses to certain stimuli (see also step S10 in FIG. 2). The analog signal processor 3 can perform processings such as amplification, filtering, etc., as needed. An analog EEG signal is output from the analog signal processor 3 signal to an analog to digital (A/D) converter 5 on a signal line 4. The analog to digital converter 5 converts the analog EEG signal into a digital form that can be used to provide a graphical representation of the test subject's responses to viewing the video data on the TV monitor 11 (see step S15 in FIG. 2).

The A/D converter 5 has a bidirectional signal line 6 connecting the A/D converter 5 with a computer 7. This bidirectional signal line 6 allows the computer 7 to accurately synchronize the collection of test data and the activation of the test stimuli as discussed below.

The accurate synchronization of the test stimuli and collection of data is enabled by the inclusion of a switch SW8 located within the A/D converter 5 and a switch SW23 in a source audio-video device 9. When the test operator (not shown) commences the test, the operator, by, e.g., depressing a button or clicking on a mouse, signals the beginning of the test. If the operator had to then manually activate a source audio-video device 9, such as a video cassette recorder that acts as the source of the stimuli, i.e. the video data, for the subject, there could be a discrepancy in the synchronization of the data collected and the stimuli to which the test subject is responding. The present invention eliminates this possibility because the switch SW8 in the A/D converter 5 receives a signal over bidirectional signal line 6 from the computer 7 (see step S50 in FIG. 2). Activation of the switch SW8 then further results in sending a signal from AID converter 5 over signal line 10 to the switch SW23 of the source audio-video device 9 to activate the source audio-video device 9 and commence the presentation of the video data, i.e., the stimuli, to the test subject (see step S20 in FIG. 2).

At the same instant in time, the computer 7 begins collecting digital EEG data from A/D converter 5 over bidirectional signal line 6. Thus, the test operator with one simple motion simultaneously activates the collection of EEG data and activates the display of stimuli from the audio-video source 9. A precisely synchronized method of providing stimuli and collecting test subject data is thus achieved.

The source audio-video device 9 can be a conventional video cassette recorder (VCR) with one significant modification. The source audio-video device 9 includes the additional switch SW23 which receives a signal from the A/D converter 5. This switch SW23, as noted above, activates the source audio-video device 9 based on a signal received from AID converter 5 to send the audio-video signal to the TV monitor 11.

That is, upon activation of the audio-video source 9 through switch SW23, the output of the audio-video source 9 is sent to the display monitor 11 over signal line 12; that output is the video data that is viewed by the test subject being monitored by monitor 1 (see step S30 in FIG. 2). The test subject observes the display monitor 11 and passively responds to the stimuli to provide the raw analog EEG signal that is further processed as noted above.

While the audio-video source 9 outputs a signal to the display monitor 11 over signal line 12, the audio-video source 9 simultaneously sends the video component of the output signal to the computer 7 over signal line 13 (see step S25 in FIG. 2). Also simultaneously, the audio-video source 9 outputs the audio component of the output signal to a destination A/V recording device 14, which also can be a standard video cassette recorder (VCR), over signal line 15 (see step S40 in FIG. 2). The audio component of the output signal can also be fed through the computer 7, if desired.

The computer 7 is now simultaneously receiving digital EEG data from A/D converter 5 from bidirectional signal line 6 (see step S45 in FIG. 2) and the video component of the A/V source 9 signal from signal line 13 (see step S55 in FIG. 2). The computer 7 is equipped with appropriate software that processes both signals simultaneously. The computer processes the digital EEG signal from the A/D converter 5 into a graphical representation of the test subject's responses to the source stimuli. This graphical representation of the test subject's responses can take various forms but a preferred form may be a graph showing peaks (higher brain activity levels) and valleys (lower brain activity levels) that represent the test subject's interest to the stimuli representing specific brain activity as a function of time. The computer 7 is also simultaneously processing the video component of the A/V source 9 signal from signal line 13. In addition to processing these signals, the computer 7 is also processing data relating to test parameters or control data such as test time and date, demographic data of the test subject, and other relevant control data.

The computer 7 then outputs a video signal that combines the three separate data sources (i.e., the graphical representation of the digital EEG data, the video component of the A/V source 9 signal, and the test parameter and control data) into a composite VGA signal over signal line 16 (see step S60 in FIG. 2). This composite signal is sent over signal line 16 to a VGA/video converter 17 that processes the composite signal and produces two output signals. This VGA/video converter 17 can also be an integral part of the computer 7. One output signal from VGA/video converter 17 is a VGA signal that is sent to the computer monitor 19 over signal line 18 (see step S65 in FIG. 2). The computer monitor 19 can then display, e.g. in three separate windows, 1) the graphical representation of the digital EEG signal, 2) the video component of the A/V source 9, and 3) test parameter and control data. The VGA/video converter 17 simultaneously sends a video signal having the same three window displays over signal line 20 to the destination A/V recording device 14 (see step S70 in FIG. 2). This computer monitor 19 is provided for a test giver to monitor the testing. The computer 7, VGA signal line 16, VGA scan converter 17, VGA signal line 18, and computer monitor 19 collectively form a computer system 25.

The destination A/V recording device 14 is now simultaneously receiving the composite video signal from VGA/video converter 17 over signal line 20 and the audio signal from A/V source 9 over signal line 15. The destination A/V recording device 14 simultaneously records both signals to produce an overlapping and synchronized recording (e.g. on a video cassette tape or other recorded media) that captures the processed graphical representation of the digital EEG signal, the A/V source stimuli, and test parameter and control data, on a single synchronized medium. This single synchronized representation of the three video signals and one audio signal can be recorded and viewed at a later date. If desired, the destination A/V recording device 14 can record the signals and simultaneously output the composite signal to a destination monitor 21 over signal line 22 (see step S75 in FIG. 2). The destination monitor 21 may be provided so that another person can view the testing, and the destination monitor 21 may be provided at a location remote from the test site.

Thus, a system and method to accurately synchronize on a single display a graphical representation of a subject's response to stimuli, a display of the stimuli to which the subject is responding, and other data relating to test parameters, is achieved.

FIG. 2 is the flow chart essentially reiterating the paths that the various signals follow in order to produce a synchronized representation of the test data. The flow chart also shows the monitor 1 that obtains raw EEG data from the test subject (step S5). The raw EEG data is sent via signal line 2 to the analog processor 3 that sends the processed signal (step S10) via signal line 4 to the A/D converter 5 to convert the signal to a digital EEG signal (step S15). The bidirectional signal line 6 connects the computer 7 to the A/D converter 5. The computer 7 sends an activation signal to the switch SW8 in the AID converter 5 (step S50). The activation of the switch SW8 by the computer 7 results in sending a signal from the switch SW8 to the switch SW23 of the A/V source 9 via signal line 10 to begin presentation of the stimuli to the test subject (step S20). The A/D converter 5 is simultaneously sending digital EEG data obtained from the test subject to the computer 7 via bidirectional signal line 6. Thus, the presentation of stimuli to the test subject and the collection of EEG data by the computer 7 are automatically synchronized.

Now that the A/V source 9 has been activated, it sends an A/V signal to the display monitor 11 via signal line 12 so that the test subject can view the A/V stimuli (step S30). At the same time, the A/V source 9 sends a video signal via signal line 13 to the computer 7 for further processing (step S25). Also at the same time, the A/V source 9 sends an audio signal to the destination A/V recording device 14 via signal line 15 (step S40).

At this time, the computer 7 is simultaneously receiving a video signal from the A/V source 9 (step S55) and digital EEG data from the A/D converter 5 (step S45). The computer 7 processes the digital EEG data, the video signal from the A/V source 9, and other test parameter and control data stored in the computer to produce a composite video signal having, e.g., three windows to display the various aspects of the composite video signal (step S60). The computer 7 sends this composite video signal via signal line 16 to the VGA/video converter 17.

The VGA/video converter processes the signal and sends a VGA signal via signal line 18 to computer monitor 19 so that the test operator can monitor the operation of the test (step S65). At the same time, the VGA/video converter 17 is sending a composite video signal via signal line 20 to the destination A/V recording device 14 (step S70). The destination A/V recording device 14 is now simultaneously receiving the audio signal from the A/V source 9 via signal line 15 and the composite video signal from the VGA/video converter via signal line 20 (step S75). The destination A/V recording device 14 can now record a synchronized composite audio-visual representation of the graphical representation of the processed EEG data, the stimuli observed by the subject, and test parameter and control data. If desired, the synchronized composite A/V representation of this data can be recorded and viewed at a later time or can be recorded and output to a destination monitor 21 via signal line 22.

Thus, a real time synchronized and overlapped audio-visual representation of the graphical representation of the processed EEG data, the stimuli observed by the test subject, and test parameter and control data is achieved.

FIG. 3 illustrates a preferred embodiment of an output display 30 of the present invention. The output display 30 can be observed on the computer monitor 19 or the destination monitor 21. The visual display on both monitors 19, 21 is the same. The display can include three windows 31–33. Window 33 is an area where the graphical representation of the processed EEG data obtained from the computer 7 is displayed. Window 32 is an area where the A/V source 9 stimuli signal, i.e. the video data, that the test subject observed is displayed. Window 31 is the area where the test parameter and control data from the computer 7 is displayed. The integration of windows 31–33 into a single, synchronized display provides an efficient and easily reviewable presentation so that a person reviewing the results of a test can readily ascertain the test subject's responses to various stimuli.

FIG. 3 only shows one example of a format that an output display can take. The display can clearly take other formats such as, but not being limited to, deleting the output and controls window 31, spreading out the contents of the output and controls window 31, changing the positioning and size of the source video window 32 and the EEG data chart window 33, adding a video feed of the test subject, as the test subject is monitored, in the output and controls window 31, etc.

Moreover, a result of utilizing the system of the present invention is that a final product is a composite data recording file which synchronizes stimuli which a test subject was subjected, the test subject's response to that stimuli, and any other necessary control data. The result is that a resulting composite data file is generated which may be utilized in many other types of useful processings. For example, someone evaluating test results can combine plural of such composite data files from many test subjects into one larger composite file, can compare such files with other data, etc. Thus, one further benefit of the present invention is providing a single file composite data with different information which can be further processed as desired.

Further, it is noted that the computer 7 includes computer codes which execute the controls as discussed above. The computer codes can be written in any language well known to those of ordinary skill in the art.

The present invention as discussed above has also focused on the example of monitoring a test subject to detect their EEG response in relation to the test subject viewing video data. The present invention can clearly be applied to a test subject being subjected to different stimuli, such as an audio presentation, or any other sensory stimuli. Also, the information monitored from the test subject is clearly not limited to EEG data but can include many different kinds of data such as EKG data, heart rate, blood pressure, body temperature, galvanic skin response, pupil dilation, etc. In certain of these instances, the present invention can also find many types of medicinal or therapeutic uses.

The present invention has also provided an example where video data and EEG data generated in response to a test subject viewing that video data are both recorded on a video tape in a destination VCR 14. Clearly the present invention can record any type of stimuli and the test subject response to the stimuli in any manner, including recording such data on an optical disk, a magnetic disk, or any other memory system.

A system and method has been shown to effectively and accurately synchronize on a single display a graphical representation of a subject's response to stimuli, a display of the stimuli to which the subject is responding and other data relating to test parameters. Furthermore, the system and method eliminate the potential for human error in obtaining the test data.

The above-discussed operation in the present invention has focused on a system in which certain stimuli is sensed by a single test subject and the stimuli and that single test subject's response to the stimuli are overlappingly recorded. A further feature of the present invention is to generate data from a plurality of test subjects in parallel. Such data generated in parallel can be recorded individually in parallel. This provides a significant benefit of allowing a test giver to reduce the amount of time needed to obtain test data from a plurality of test subjects.

Figure 4A:
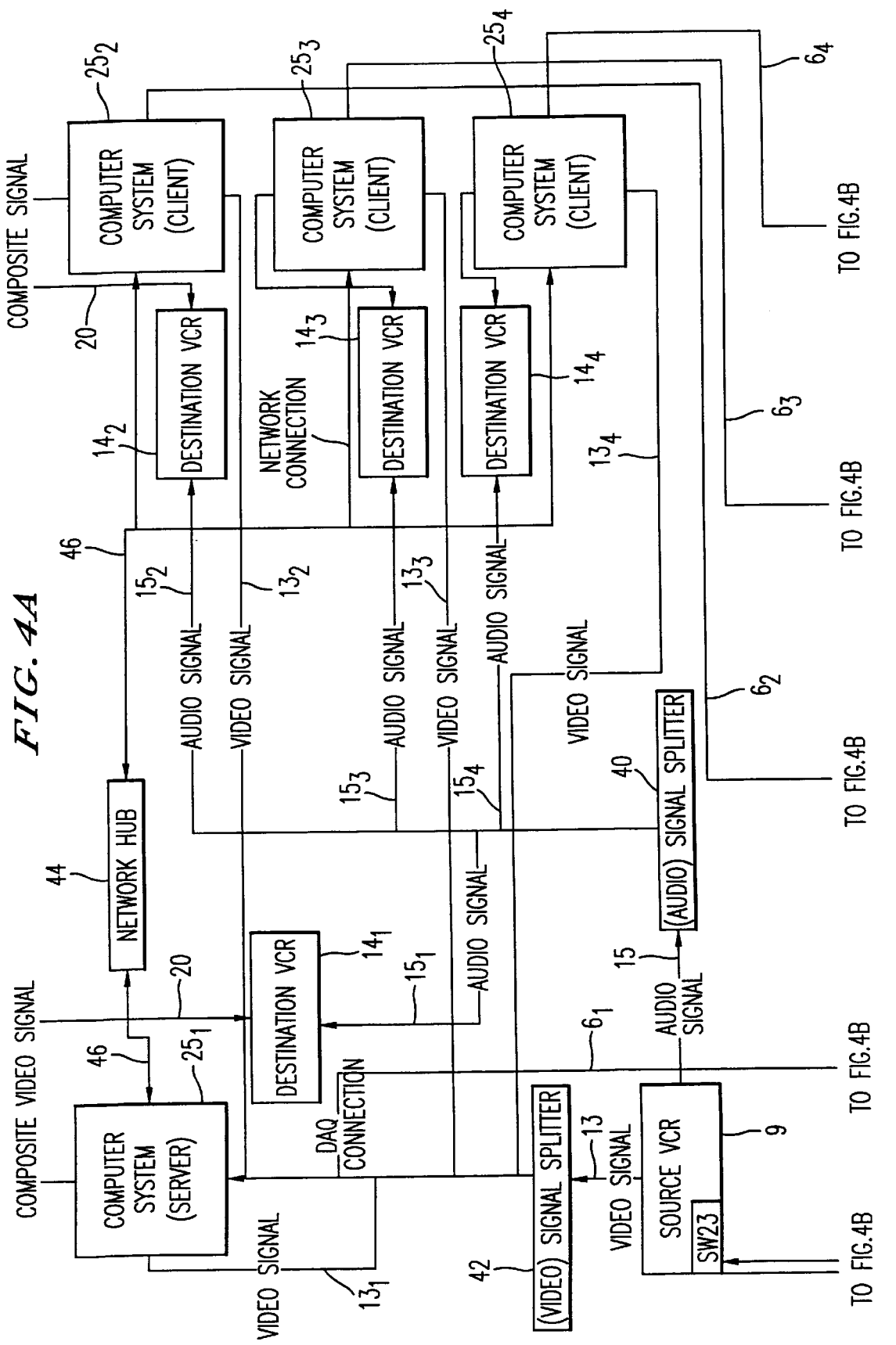
FIG. 4 illustrates a preferred embodiment of the present invention in a network system in which a plurality of test subjects can be monitored and response data from all of the test subjects is obtained in parallel.

FIG. 4 shows an embodiment of the present invention to achieve such an operation of the present invention. More particularly, the structure shown in FIG. 4 is a network system of the present invention in which a plurality of monitors $1_1$–$1_4$ are provided for a plurality of respective test subjects. In the embodiment shown in FIG. 4 four different monitors $1_1-1_4$ are shown, but of course this structure in the present invention is not limited to this number, and instances may arise when it would be desirable to monitor a larger number of test subjects simultaneously.

As shown in FIG. 4, a plurality of monitors $1_1-1_4$ are provided for a respective plurality of different test subjects. Similarly as shown in FIG. 1, connected to each monitor $1_1-1_4$ is a respective analog signal amplifier/processor $3_1-3_4$ and analog/digital converter data acquisition device $5_1-5_4$. Furthermore, one of the analog/digital converter data acquisition devices $5_1$ is connected to a source VCR 9 by a trigger switch line 10. In the example shown in FIG. 4 the left-most analog/digital converter data acquisition device $5_1$ has its switch S8 connected to the switch SW23 of the source VCR 9 to send a trigger signal 10 thereto.

The device as shown in FIG. 4 operates such that for each of the respective monitors $1_1-1_4$ a separate destination VCR $14_1-14_4$ is corresponded thereto. With such a structure in the present invention, the monitored results output from the monitor $1_1$ are recorded on the destination VCR $14_1$ in synchronization and overlapped with the signal output from the source VCR 9, similarly as in the embodiment shown in FIG. 1. Similarly, in synchronization and overlapped with the output from the source VCR 9, the monitored results from the monitor $1_2$ are recorded at the destination VCR $14_2$, the monitored results from the monitor $1_3$ are recorded at the destination VCR $14_3$, and the monitored results from the monitor $1_4$ are recorded at the destination VCR $14_4$.

The benefit of the system of FIG. 4 is that test results from a plurality of test subjects, in the examples shown in FIG. 4 from four test subjects, can be recorded in parallel. That has the significant benefit of reducing the amount of time required to obtain test results from a plurality of test subjects.

The system as shown in FIG. 4 achieves the above-noted operation by utilizing a plurality of destination VCRs $14_1-14_4$ each connected to a respective computer system $25_1-25_4$. Each respective computer system $25_1-25_4$ corresponds to a computer system 25 as shown in FIG. 1 and respectively includes a computer 7, VGA signal line 16, VGA scan converter 17, VGA signal line 18, and computer monitor 19; although it is possible for the computer systems $25_1-25_4$ to not include each of those elements. The system as shown in FIG. 4 requires that each such computer system $25_1-25_4$ is connected to a network hub 44 through a network connection line 46, which allows signals to be exchanged between the various computer systems $25_1-25_4$.

The audio signal output of the source VCR 9, i.e., the signal output on audio signal line 15, is initially fed to an audio signal splitter 40. The audio signal splitter 40 splits the audio signal on the audio signal line 15 and provides the audio signal to each of the respective destination VCRs $14_1-14_4$ through respective audio signal lines $15_1-15_4$. Further, the video signal output from the source VCR 9, i.e., the video signal output on the video is initially provided to a video signal splitter 42. The video signal splitter 42 provides the video signal to each of the respective computer systems $25_1-25_4$ through respective video signal lines $13_1-13_4$.

In the system shown in FIG. 4 one computer system must initially be designated as a server. In the example shown in FIG. 4, the computer system $25_1$, is designated as a server computer system. Of course, any of the computer systems 25 can be designated as a server. The server computer system $25_1$ operates to provide timing control signals to the other computer systems $25_2-25_4$, which are termed clients. More particularly, in the system shown in FIG. 4 the server computer system $25_1$, is connected by the DAQ connection line $6_1$, to the analog/digital converter data acquisition device $5_1$. Similarly, the client computer systems $25_2-25_4$ are connected to respective analog/digital converter acquisition devices $5_2-5_4$ by respective DAQ connection lines $6_2-6_4$. The analog/digital converter data acquisition device $5_1$ triggers the source VCR 9 to begin outputting the audio/video signal to the TV monitor 11. The server computer system $25_1$ controls that operation by the signals it outputs on the DAQ connection line $6_1$, similarly as discussed above with respect to the embodiment of FIG. 1.

At the same time that the server computer system $25_1$ indicates to the source VCR 9 to begin displaying stimuli, the server computer system $25_1$ outputs a signal to each of the computer systems $25_2-25_4$ through the network hub 44 and the network connection lines 46 indicating an operation to begin the recording of data at the respective destination VCRs $14_2-14_4$. In this instance the computer systems $25_2-25_4$ activate the respective analog/digital converter data acquisition devices $5_2-5_4$ to begin the data acquisition at the same time that the server computer system $25_1$ activates the analog/digital converter data acquisition device $5_1$ to begin data acquisition and to send the trigger signal 10 to the source VCR 9 to begin displaying the stimuli on the TV monitor 11. The data acquired from the monitors $1_2-1_4$ is then recorded at the respective destination VCRs $14_2-14_4$ along with the audio and video data output from the source VCR 9 in synchronization and overlapped under control of the computer systems $25_2-25_4$, as in the embodiment of FIG. 1.

The network hub 44 must be constructed to relay information between the server computer system $25_1$ and the computer systems $25_2-25_4$. The network hub 44 can take the form of any system which allows various computers to "talk" to each other with a communication protocol. One example of a form the network hub 44 can take is a 100 Mbit Fast Ethernet network hub of type 100 Base TX utilizing a communication protocol TCP/IP.

With the above-noted structure in FIG. 4, the monitored data from each of the monitors $1_1-1_4$ are recorded at the respective destination VCRs $14_1-14_4$ in parallel and in synchronization and overlapped with the signal output from source VCR 9. However, it is noted that the destination VCRs $14_2-14_4$ are optional in the sense that the data output from the respective monitors $1_2-1_4$, time-stump data, and optionally the corresponding source stimuli from source VCR 9, can be stored in the respective computer systems $25_2-25_4$, e.g. in hard disks in the computers 7 in the respective computer systems $25_2-25_4$, without being recorded at a destination VCR. In that case, the destination VCRs $14_2-14_4$ would not be needed. Such an operation can be executed if it is not required to provide a video recording of the test subjects monitored at monitors $1_2-1_4$.

With the structure in the present invention as shown in FIG. 4, not only is data from multiple test subjects recorded in parallel, but the data from multiple test subjects can be displayed in parallel as each of the computer systems $25_1-25_4$ can include its own computer monitor 19. Thus, a test operator can view the monitored tests results in parallel if desired, and if each of the computer systems $25_1-25_4$ is located in the same room. Of course as in the embodiment of FIG. 1 the recorded data at each of the destination VCRs $14_1-14_4$ can be retrieved and displayed.

The software needed to control the network system as shown in FIG. 4 can take many different forms. However, the software should perform the following functions. First, the software must enable one of the computer systems $25_1$–$25_4$ to be designated as a server and the other computer systems to be designated as clients. In FIG. 4 computer system $25_1$ is the server and computer systems $25_2$–$25_4$ are the clients. The client computers must also be able to be placed in a "waiting state" to await control signals from the server computer system through the network hub 44 and network connection 46. The server computer system $25_1$ then requires a start command setting such that when all of the client computer systems $25_2$–$25_4$ are in the waiting state, and the start command is executed, the server computer system $25_1$ sends a command to each of the client systems $25_2$–$25_4$ to start collecting data. The client computer systems $25_2$–$25_4$ then send signals to their respective analog/digital converter data acquisition devices $5_2$–$5_4$ to begin data collection. At the same time, the server computer system $25_1$ sends a signal to the analog/digital converter data acquisition device $5_1$ to collect data from the monitor $1_1$. At that time, the analog/digital converter data acquisition device $5_1$ sends the trigger signal 10 to the source VCR 9 to begin the output of data to the TV monitor 11.

Simultaneously with the start of data collection, the source VCR 9 also sends the audio and video signals to the respective audio signal splitter 40 and video signal splitter 42, and the audio and video signals are then provided to the respective destination VCRs $14_1$–$14_4$ through audio signal lines $15_1$–$15_4$ and video signal lines $13_1$–$13_4$. The destination VCRs $14_1$–$14_4$, under the control of the respective computer systems $25_1$–$25_4$, then control the recording of data from the source VCR 9 in synchronization and overlapped with the monitored data from the respective monitors $1_1$–$1_4$.

Obviously, numerous additional modifications and variations of the present invention are possible in light of the above teachings. It is therefore to be understood that within the scope of the appended claims, the present invention may be practiced otherwise than as specifically described herein.

What is claimed as new and desired to be secured by Letter Patent of the United States is:

1. A system, comprising:
    a source configured to provide input stimuli to a plurality of test subjects;
    a plurality of monitors each configured to monitor a reaction of a respective of the plurality of test subjects to the input stimuli; and
    a controller configured to generate, for each of the plurality of monitors, a composite signal including the input stimuli and the monitored reaction of the respective of the plurality of test subjects to the input stimuli in synchronization.

2. A system according to claim 1, wherein the controller is further configured to control recording of the respective generated composite signals onto respective recording mediums.

3. A system according to claim 1, wherein the controller is further configured to display the respective generated composite signals on respective monitors.

4. A system according to claim 2, wherein the controller is further configured to retrieve the respective recorded generated composite signals from the respective recording mediums and to display the respective retrieved composite signals on respective monitors.

5. A system according to claim 1, wherein the input stimuli is a video signal and the respective monitored reactions of the plurality of test subjects to the input stimuli includes EEG data.

6. A system according to claim 2, wherein the input stimuli is a video signal and the respective monitored reactions of the plurality of test subjects to the input stimuli includes EEG data.

7. A system according to claim 3, wherein the input stimuli is a video signal and the respective monitored reactions of the plurality of test subjects to the input stimuli includes EEG data.

8. A system according to claim 4, wherein the input stimuli is a video signal and the respective monitored reactions of the plurality of test subjects to the input stimuli includes EEG data.

9. A system, comprising:
    source means for providing input stimuli to a plurality of test subjects;
    monitoring means for monitoring a reaction of each of the plurality of test subjects to the input stimuli; and
    control means for generating, for the monitoring means, a composite signal including the input stimuli and the monitored reaction of a respective of the plurality of test subjects to the input stimuli in synchronization.

10. A system according to claim 9, wherein the control means further controls recording of the respective generated composite signals onto respective recording means.

11. A system according to claim 9, wherein the control means further displays the respective generated composite signals on respective display means.

12. A system according to claim 10, wherein the control means further retrieves the recorded respective generated composite signals from the respective recording means and displays the respective retrieved composite signals on respective display means.

13. A system according to claim 9, wherein the source means inputs a video signal as the input stimuli and the respective monitoring means monitors the respective reactions of the plurality of test subjects to the input stimuli to include EEG data.

14. A system according to claim 10, wherein the source means inputs a video signal as the input stimuli and the respective monitoring means monitors the respective reactions of the plurality of test subjects to the input stimuli to include EEG data.

15. A system according to claim 11, wherein the source means inputs a video signal as the input stimuli and the respective monitoring means monitors the respective reactions of the plurality of test subjects to the input stimuli to include EEG data.

16. A system according to claim 12, wherein the source means inputs a video signal as the input stimuli and the respective monitoring means monitors the respective reactions of the plurality of test subjects to the input stimuli to include EEG data.

17. A process, comprising the steps of:
    providing input stimuli to a plurality of test subjects;
    respectively monitoring a reaction of each of respective of the plurality of test subjects to the input stimuli;
    generating, for each of the respective steps of monitoring a reaction of respective of each of the plurality of test subjects, a respective composite signal including the input stimuli and the monitored reaction of a respective of the plurality of test subjects to the input stimuli in synchronization.

18. A process according to claim 17, further comprising the step of recording the respective generated composite signals onto respective recording mediums.

19. A process according to claim 17, further comprising the step of displaying the respective generated composite signals on respective monitors.

20. A process according to claim 18, further comprising the steps of retrieving the recorded respective generated composite signals from the respective recording mediums and displaying the respective retrieved composite signals on respective monitors.

21. A process according to claim 17, wherein in the input step the input stimuli is a video signal and in the monitoring step the respective monitored reactions of the plurality of test subjects to the input stimuli includes EEG data.

22. A process according to claim 18, wherein in the input step the input stimuli is a video signal and in the monitoring step the respective monitored reactions of the plurality of test subjects to the input stimuli includes EEG data.

23. A process according to claim 19, wherein in the input step the input stimuli is a video signal and in the monitoring step the respective monitored reactions of the plurality of test subjects to the input stimuli includes EEG data.

24. A process according to claim 20, wherein in the input step the input stimuli is a video signal and in the monitoring step the respective monitored reactions of the plurality of test subjects to the input stimuli includes EEG data.

25. A computer program product, comprising:

a computer storage medium and a computer program code mechanism embedded in the computer storage medium for causing a computer to control a source configured to provide input stimuli to a plurality of test subjects and for causing a computer to control a plurality of monitors configured to respectively monitor a reaction of respective of each of the plurality of test subjects to the input stimuli, the computer program code mechanism including:

a first computer code configured to generate, for each of the respective plurality of monitors, a respective composite signal including the input stimuli and the monitored reaction of a respective of the plurality of test substrates to the input stimuli in synchronization.

26. A computer program product according to claim 25, wherein the computer program code mechanism further comprises a second computer code configured to control recording of the respective generated composite signals onto respective recording mediums.

27. A computer program product according to claim 26, wherein the computer program code mechanism further comprises a second computer code configured to display the respective generated composite signals on respective monitors.

28. A computer program product according to claim 26, wherein the computer program code mechanism further comprises a third computer configured to retrieve the recorded respective generated composite signals from the respective recording mediums and to display the respective retrieved composite signals on respective monitors.

29. A computer program product according to claim 25, wherein the input stimuli is a video signal and the respective monitored reactions of the plurality of test subjects to the input stimuli includes EEG data.

30. A computer program product according to claim 26, wherein the input stimuli is a video signal and the respective monitored reactions of the plurality of test subjects to the input stimuli includes EEG data.

31. A computer program product according to claim 27, wherein the input stimuli is a video signal and the respective monitored reactions of the plurality of test subjects to the input stimuli includes EEG data.

32. A computer program product according to claim 28, wherein the input stimuli is a video signal and the respective monitored reactions of the plurality of test subjects to the input stimuli includes EEG data.

* * * * *